United States Patent [19]

Isoldi

[11] 4,252,785

[45] Feb. 24, 1981

[54] CONTROLLED RELEASE COMPOSITION

[75] Inventor: Donald J. Isoldi, Nutley, N.J.

[73] Assignee: Hexcel Corporation, San Francisco, Calif.

[21] Appl. No.: 56,122

[22] Filed: Jul. 9, 1979

[51] Int. Cl.[3] .......................... A61K 9/22; A61K 9/26; A61K 31/115; A61K 31/785

[52] U.S. Cl. ...................................... 424/19; 424/22; 424/82

[58] Field of Search ............... 260/29.4 R; 424/19–22, 424/32, 36, 8.82

[56] References Cited

U.S. PATENT DOCUMENTS

| | | | |
|---|---|---|---|
| 795,757 | 7/1905 | Blackmore | 424/82 |
| 1,408,535 | 3/1922 | Ressler | 424/76 |
| 2,490,958 | 12/1949 | Graenacher et al. | 424/82 |
| 2,491,287 | 12/1949 | Smith et al. | 424/82 |
| 2,541,248 | 2/1951 | Hibbs | 424/76 |
| 2,700,683 | 1/1955 | Tesoro et al. | 424/76 |
| 2,851,424 | 9/1958 | Switzer et al. | 260/39 R |
| 3,074,845 | 1/1963 | Geary | 424/32 |
| 3,076,744 | 2/1963 | Geary | 424/82 |
| 3,102,108 | 8/1963 | Aebi | 424/82 |
| 3,162,573 | 12/1964 | Geary | 424/82 |
| 3,183,200 | 5/1965 | Henson | 260/29.4 R |
| 3,223,513 | 12/1965 | Geary | 424/82 |
| 3,516,846 | 6/1970 | Matson | 424/32 |
| 3,584,113 | 7/1971 | Takebe et al. | 424/19 |
| 4,018,741 | 4/1977 | Renner | 260/29.4 R |
| 4,160,754 | 7/1979 | Schapel et al. | 424/82 |

FOREIGN PATENT DOCUMENTS

| | | | |
|---|---|---|---|
| 697623 | 10/1964 | Canada | 424/82 |
| 1936748 | 1/1970 | Fed. Rep. of Germany | 424/82 |
| 524125 | 7/1940 | United Kingdom | 424/82 |
| 587263 | 12/1944 | United Kingdom | 424/82 |
| 920524 | 3/1963 | United Kingdom | 424/82 |

OTHER PUBLICATIONS

C.A. 44: 3204f, (1950), 49, #11304h, (1955), 51, #13269b, (1957), 53, #737f, (1959), #9585, (1959), 54, #23212q, (1960), C.A. 54, #25909e, (1960), 55, #23840h, (1961), 61, #84469, (1964), 62, #5150d, (1965), 63, #5532f, (1965), 73, #67857k, (1970), C.A. 75, #121418z, (1971), 86, #173455f, (1977), 87, #54890e (1977).

Haler et al., Nature 190, (4777): 734–735, May 20, 1961 A New Highly Effective but Non-Toxic Antibacterial Substance.

C.A. 41: 7642b, (1947), 45 #3989b, (1951), 49 #15153q, (1955), 51, #17066c, (1957), 51, #2221c, (1957), C.A. 52, #12307a, (1958), C.A. 61: 15286d, (1964), 62, #5825f, (1965), 70, #67050e, (1969), C.A. 72, #91272r, (1970), 78, #80891q, 8 (1973), 79, #101721x, (1973).

*Primary Examiner*—Shep K. Rose
*Attorney, Agent, or Firm*—Jacobs & Jacobs

[57] ABSTRACT

A microporous controlled release composition, comprising at least about 20%, by weight, based on the total weight of the composition, of a solid, low molecular weight urea-formaldehyde resin having a molar ratio of urea to formaldehyde of from about 2:1 to about 3.5:1, and at least one active material contained in and releasable from said resin over a sustained period of time when said resin is in an aqueous medium.

9 Claims, No Drawings

CONTROLLED RELEASE COMPOSITION

The present invention relates to controlled release compositions, and more particularly to a low molecular weight urea-formaldehyde resin containing active materials that are released at a controlled rate in aqueous media, and to a method of producing the same.

Controlled release systems are widely used in the home and industry, e.g. for air fresheners, for sustained release of germicides into toilet systems, and for other uses where gradual release of a dye, deodorant, or other releasable "active ingredients" is desired. Existing systems employ complex and hence costly matrices to hold and slowly release the active ingredient. Generally, such products are prepared by the "hot melt" process, in which the various components are made molten, poured into molds and cooled. It has now been discovered that a urea-formaldehyde resin can be used as a matrix for a controlled release system, with economies in both raw materials and production.

Thus, the present invention provides a controlled release composition, comprising at least about 20% by weight, based on the total weight of the composition, of a solid, low molecular weight urea-formaldehyde resin having a molar ratio of urea to formaldehyde of from about 2:1 to about 3.5;1, and at least one active material contained in and releasable from said resin over a sustained period of time when said resin is in an aqueous medium.

Urea-formaldehyde resins (hereinafter "U-F resins") are poly(alkylene amides) prepared by reacting urea with a molar excess of formaldehyde at alkaline pH, followed by heating the solution thus formed in the presence of an acidic catalyst to form the final product. The final products are used as adhesives, molding powders, textile finishing agents and laminating resins. These resins also have a variety of specialized uses. When used as a molding powder, a primary attribute of the U-F resin has been its hardness and relative chemical inertness.

None of the prior uses of U-F resins suggest its application to controlled release systems. Indeed, the hardness of prior U-F resins would prevent the controlled diffusion of active ingredients out of the resin, particularly from the interior. The present invention is based on the use of a solid, low molecular weight U-F resin having a molar ratio of urea to formaldehyde of from about 2:1 to about 3.5:1. In contrast with prior art industrial U-F resins that traditionally employ a molar excess of formaldehyde, the U-F resins employed in the present invention employ a molar deficiency of formaldehyde.

Preparation of the U-F resins used in the present invention is simple, efficient and, surprisingly, exceptionally rapid. Urea is mixed with formaldehyde in a suitable solvent at slightly alkaline pH, say about pH 8 to about 9, and heated gently with stirring to dissolve the urea. Conveniently, the formaldehyde is added as an aqueous or alcoholic solution, which then provides the solvent for the urea. Commercial grade urea prills and commercial 37-50% aqueous solutions or 40% alcoholic solutions of formaldehyde are desirably employed. After formation of the solution of urea-formaldehyde reaction product, the releasable ingredients are added and an acidic catalyst is then added to initiate polymerization.

Polymerization rapidly occurs at room temperature with a slight exotherm. The polymerizate may be stirred, if desired, to accelerate polymerization. Surprisingly, the use of organic acids, as for example carboxylic or sulfonic acids, accelerates the polymerization so rapidly that the polymerizate sets up to a solid mass in under 60 seconds with mild heating, and even faster with stirring. Full cure is obtained within 30 minutes, often in as little as 5-10 minutes.

Polymerization time is inversely proportional to the concentration of active ingredients and diluents in the polymerizate and directly proportional to temperature. A polymerizate containing 50% by weight urea-formaldehyde reaction product and 50% of a mixture of active ingredients and diluents will solidify in 30-60 seconds when heated to 32°-42° C. after adding the catalyst. Control over polymerization times for other polymerizates is readily determined empirically using the time-temperature relationships set forth in Table I below:

TABLE I

| Temperature | Reaction Time to Solidify |
|---|---|
| 52° C. | 20 to 30 seconds |
| 42° C. | 30 to 40 seconds |
| 32° C. | 45 to 60 seconds |
| 22° C. | 60 to 75 seconds |

Control over the molar ratio of urea to formaldehyde is important to the success of the present invention. Table II below illustrates the effect of changes in this molar ratio based on several series of polymerizations carried out by reacting urea prills with 37% aqueous formaldehyde at pH 8-9 in the molar ratios noted, and then adding formic acid to the polymerizate warmed to 45°-50° C. No active ingredient or diluent was employed, and the total amount of urea and formaldehyde was from about 2.6 to 4 mols.

TABLE II

| Molar Ratio Urea: Formaldehyde | Remarks |
|---|---|
| 0.33 to 0.50:1 | Liquid to soft paste. |
| 0.60:1 to 1.8:1 | Semi-solid to solid; violent exotherm; explosions have been encountered at molar ratios of 1:1, 1.4:1 and 1.5:1. |
| 2.0:1 to 3.0:1 | Rapid formation of hard, white solid block. |
| 3.0:1 to 3.5:1 | Harder product. |
| above 3.5:1 | Difficult to dissolve reactants in solvent; difficult to control reaction; product too hard. |

Table II shows that below the minimum molar ratio of 2:1, the product is a useless liquid formed under very unstable and often explosive conditions. Above a molar ratio of 3.5:1, the product is too hard to permit diffusion from the interior, and is also difficult to form. The preferred molar ratio is from about 2:1 to less than about 3:1, most preferably from about 2:1 to about 2.8:1.

Catalysts useful in preparing the U-F resins according to the invention are any hydrogen ion donors used as amino resin catalysts, such as salts of weak bases and strong acids, e.g. aluminum sulfate, mineral acids, e.g. HCl, $H_2SO_4$ etc., carboxylic acids, e.g. formic acid, acetic acid, oxalic acid, adipic acid, citric acid, salicylic acid and the like, sulfonic acids, e.g. paratoluene sulfonic acid and the like, phosphoric acid, etc. Presently preferred is paratoluene sulfonic acid due to its ease of handling and safety in use. For convenience, the solid paratoluene sulfonic acid may be used as a 67 to 70% aqueous solution. Generally, 0.5 to 10 parts of catalyst per 100 parts of U-F resin will be sufficient.

The "active material" may be any material that is desired to be released from the U-F resin in aqueous media at a controlled rate. Hydrophillic materials are usable as such, and hydrophobic materials are usable in combination with a surfactant. Accordingly, there is virtually no limitation on the active material employed, Suitable active materials include detergents, germicides, such as quanternary ammonium salts, deodorizers, reactants etc. Fragrances may also be used, as well as dyes for color and/or for determining when the life of controlled release composition is nearing its end. Where the active material is hydrophobic, surfactants, normally non-ionic surfactants, are employed to put the hydrophobic material into solution in the polymerizate. The surfactant also contributes to the cleaning action of the composition.

The "diluent" is employed to control the release rate of the composition, this rate being inversely proportional to the amount of diluent and directly proportional to the amount of releasable material. The diluent may be releasable if its release has no adverse affect on the system. Suitable diluents include water, organic liquids, such as glycols, inert fillers and the like. For optimum results, it is presently desired that the composition contain at least about 20% by weight U-F resin, preferably from about 35 to about 90%, U-F resin and most preferably from about 50 to about 80% U-F resin, by weight, based on the total weight of the composition. When the amount of U-F resin exceeds about 90%, the release rate becomes quite slow, whereas below about 20% the composition becomes a soft paste and hence requires a special container. The amount of active material will be empirically determined, but generally at least about 20% will be used. Generally, at least 50% U-F resin, up to about 25% active material and up to 25% diluent, all by weight, based on the total weight of the composition, will be employed, with the maximum amount of U-F resin being 90%, as discussed above. A preferred long-lasting composition comprises from about 50 to about 80% by weight of said urea-formaldehyde resin, up to about 15% by weight of said active material, based on the total weight of the composition, and the balance being said diluent, the molar ratio of urea to formaldehyde in said resin being from about 2:1 to about 2.8:1, most preferably about 2:1.

The present invention is ideally suited to mass production of controlled release compositions for sanitizing and deodorizing industrial and household toilet systems, both recirculating and non-recirculating systems. In recirculating systems, the sanitizing composition is generally changed daily. In non-recirculating systems, toilet cleaners and urinal blocks are intended to last for a period of weeks. For example, conventional urinal blocks of para-dichlorobenzene have a life of about two to four weeks. Controlled release compositions can be tailored to have a life of from a few hours to several weeks, as desired, by control over the amounts of active materials and diluent as described above. With any composition according to the invention, comes the important advantage of economic manufacture. Thus, metered amounts of polymerizate can be fed into a succession of plastic or metal containers moving on an assembly line, by means of two nozzles in series, one feeding the catalyst and the other a solution of U-F resin prepolymer containing the active ingredients and diluent. In 30–60 seconds, the mass will polymerize in situ thus giving rise to economics of manufacture not possessed by the hot melt process. Furthermore, the use of subliming chlorinated aromatics is totally avoided.

Presently preferred controlled release compositions of the invention for sanitizing toilet systems are as follows:

TABLE III

|  | 24-Hour Release (g.) | Long-lasting Toilet Bowl or Urinal Block (g.) |
| --- | --- | --- |
| U.F. Resin** | 21.3 | 59.8 |
| Fragrance | 2.5 | 4 |
| Germicide | 9.7 | 4 |
| Surfactant (non-ionic) | 2.5 | 4 |
| Solid diluent*** | 11.4 | — |
| Organic diluent | 2.5 | 4 |
| Water | 7.2 | 24.2 |

**U-F resin molar ratio urea: formaldehyde = 2:1
***based on 9.2g. diluent + 2.2g. solid catalyst Any germicide active in aqueous media may be used in the controlled release composition of the invention. Preferably, the germicide is a quanternary ammonium salt, such as cetyl dimethyl ethyl ammonium bromide or chloride, cetyl pyridinium chloride, alkyl dimethyl benzyl ammonium chloride, myristol trimethyl ammonium bromide and the like. See also U.S. Pat. No. 3,884,977 of Nicholas M. Molnar, which describes other useful quanternary ammonium salts as germicides. Presently preferred is "Germitol", an alkyl dimethyl benzene ammonium chloride containing 65% $C_{12}$, 25% $C_{14}$ and 10% $C_{16}$ as the alkyl moiety. Germitol is sold as a paste containing 97–100% active germicide or as a 50% aqueous solution.

Other useful germicides are halogenated salicylanilides, carbanilides or thiocarbanilides having one or two halogen atoms on each phenyl ring and up to one trifluoromethyl on one phenyl ring. Preferably, the halogen atom is chlorine or bromine. These materials are well known to the art and include such species as 3,4′, 5-tribromo salicylanilide, 3,5-dibromo salicylanilide, 4′, 5-dibromo salicylanilide, 5-chloro-2′,4′-dibromo salicylanilide, 3,4′, 5-trichloro salicylanilide, 4′-chloro-5-bromo salicylanilide, 2′,3,4′,5-tetrabromo salicylanilide, 3,4,4′-trichlorocarbanilide and 3-trifluoromethyl-4,4′-dichloro carbanilide. Also useful are halogenated 2-hydroxy-diphenyl ethers having one or two halogen atoms on each phenyl ring. Preferably, the halogen atoms are chlorine or bromine. Such halogenated 2-hydroxydiphenyl ethers are well known and described in greater detail in, for example, U.S. Pat. No. 3,506,720. Preferred species of this class include 2,4,4′-trichloro-2′-hydroxydiphenyl ether and 4,4′-dichloro-2′-hydroxydiphenyl ether. Alternatively, halogenated 2-hydroxydiphenyl bisphenols may be used, such as 3,3′-dibromo-2,2′-biphenyldiol, 3,3′,5,5-tetrabromo-2,2′-biphenyldiol, 3,3′,5,5′-tetrabromo-4,4′-biphenyldiol, octachloro-2,2′-biphenyldiol, 2,2′,6,6′-tetrabromo-3,3′-biphenyldiol, and 2,2′,6,6′-tetrabromo-4,4′-biphenyldiol.

The present invention is illustrated by the following Examples. All parts and proportions referred to in this specification and in the appended claims are by weight, unless otherwise specified.

EXAMPLE I

A deodorizing block for urinals is prepared by charging 48 grams of urea prills (commercial grade) with 32 grams of a 37% aqueous formaldehyde solution and two drops of triethanolamine to provide a pH of 8-9, into a flask equipped with a magnetic stirrer. The contents of the flask were stirred under heating to 40°-50° C. for about 30 minutes until a clear solution at 45°-50° C. was obtained. Four grams of each of the following was then charged to the flask with stirring:

|  |  |
|---|---|
| Germitol | 4 |
| Pine fragrance | 4 |
| Non-ionic surfactant | 4 |
| Water | 4 |
| Propylene glycol | 4 |

The clear solution thus obtained, at a temperature of 45° C., was poured into small aluminum cups containing paratoluene sulfonic acid in an amount of 2 grams per 100 grams of solution. Polymerization commences virtually instantaneously, with a slight exotherm to about 70° C. A solid block is obtained in 30-60 seconds, sooner with stirring.

The microporous controlled release composition is an excellent urinal block possessing germicidal and deodorizing properties. When tested in a conventional urinal, it had a life of four weeks. Other experiments showed that the life could be extended by using a larger amount of each ingredient.

EXAMPLE 2

Using the procedure of Example 1, two samples of a circulating toilet block were prepared, sample A having a weight of 24.7 grams and sample B having a weight of 57.0 grams. The formulation below was used for samples A and B, the only difference being the weight of the samples:

| Formulation | % |
|---|---|
| Urea prills | 30 |
| Formaldehyde (37% aqueous solution) | 20 |
| Sodium sulfate | 16 |
| Aluminum sulfate | 4 |
| Concentrate "X" | 30 |
|  | 100 |

Sodium sulfate was used as a solid filler and aluminum sulfate was used as catalyst. Concentrate "X" was:

|  | % |
|---|---|
| Germitol | 57.1 |
| Pine Fragrance | 14.3 |
| Non-ionic surfactant | 14.3 |
| Hexylene glycol | 14.3 |
|  | 100.0 |

To determine the rate of release, each Sample was placed in a five gallon jar containing 16 liters of water. The water was stirred throughout each test. Samples of water were taken periodically and titrated with 0.02 N sodium tetraphenyl boron and dichlorofluorescein as indicator to determine the concentration of Germitol in the water. The results are reported in Table IV below:

TABLE IV

| TIME | CONCENTRATION OF GERMITOL (ppm) | |
|---|---|---|
| HOURS | SAMPLE A | SAMPLE B |
| 0 | 0 | 0 |
| 1 | 52.0 | 52.0 |
| 2 | 75.0 | 75.0 |
| 3 | 113.0 | 90.0 |
| 4 | 130.0 | 105.0 |
| 5 | 172.0 | 127.0 |
| 6 | 210.0 | 150.0 |
| 7 | 232.0 | 180.0 |
| 8 | 278.0 | 202.0 |
| 9 | 300.0 | 224.0 |
| 10 | 310.0 | 300.0 |
| 12 | 310.0 End | 450.0 |
| 14 |  | 480.0 |
| 16 |  | 525.0 |
| 18 |  | 645.0 |
| 24 |  | 700.0 |
| 25 |  | 700.0 End |

Table IV illustates that the life of the release composition is readily controlled.

The non-ionic surfactant used in Examples 1 and 2 was "Igepal CO-630" (GAF Corporation), a nonyl phenoxy (ethyleneoxy) ethanol of the formula

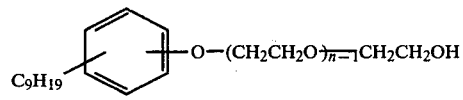

where n=9, but surfactants where n=6 to 10 are generally useful.

What is claimed:

1. A microporous controlled release composition in the form of a solid block, comprising from about 20% to about 90% by weight, of a solid, low molecular weight urea-formaldehyde resin having a molar ratio of urea to formaldehyde of from about 2:1 to about 3.5:1, at least about 4% by weight up to about 25%, by weight, of an active material comprising a germicide contained in and releasable from said resin over a sustained period of time when said resin is in an aqueous medium, all based on the total weight of the composition, and the balance, if any, being a diluent.

2. The composition according to claim 1, wherein said urea to formaldehyde molar ratio is from about 2:1 to less than about 3:1.

3. The composition according to claim 2, wherein said molar ratio is from about 2:1 to about 2.8:1.

4. The composition according to claim 1, wherein said urea-formaldehyde resin comprises from about 50 to about 80% by weight, based on the weight of said composition.

5. The composition according to claim 1, wherein said active material is at least one further material selected from the group consisting of detergents, deodorizers, fragrances and dyes.

6. The composition according to claim 1, comprising from about 50 to about 80% by weight of said urea-formaldehyde resin, up to about 15% by weight of said active material, based on the total weight of said composition, and the balance being said diluent, the molar ratio of urea to formaldehyde in said resin being from about 2:1 to about 2.8:1.

7. The composition according to claim 6, wherein said molar ratio is about 2:1.

8. The composition according to claim 1, wherein said germicide is a quaternary ammonium salt.

9. The composition according to claim 1, wherein said active material comprises a germicide, a detergent and a fragrance.

* * * * *